United States Patent
Ito

(10) Patent No.: US 7,140,882 B2
(45) Date of Patent: Nov. 28, 2006

(54) METHOD OF PRODUCING LOW MOLECULAR WEIGHT CHITIN/CHITOSAN AND METHOD OF PRODUCING AN OSTEOCONDUCTION SUBSTANCE

(75) Inventor: Michio Ito, Nagano (JP)

(73) Assignee: Matsumoto Dental University, Nagano (JP)

( * ) Notice: Subject to any disclaimer, the term of this patent is extended or adjusted under 35 U.S.C. 154(b) by 0 days.

(21) Appl. No.: 10/277,928

(22) Filed: Oct. 23, 2002

(65) Prior Publication Data

US 2003/0078394 A1    Apr. 24, 2003

(30) Foreign Application Priority Data

Oct. 24, 2001    (JP)  ............................... 2001-326465

(51) Int. Cl.
     *A61K 31/722*    (2006.01)
     *A61K 2/28*    (2006.01)
     *A61K 5/09*    (2006.01)

(52) U.S. Cl. ................. 433/212.1; 424/42.1; 424/42.5; 514/55; 623/23.51; 623/23.61

(58) Field of Classification Search ............... 514/55; 536/20, 124; 424/424, 425; 433/212.1; 623/23.51, 23.61
See application file for complete search history.

(56) References Cited

U.S. PATENT DOCUMENTS 5,618,339 A * 4/1997 Ito ........................ 106/124.3

6,417,247 B1 * 7/2002 Armstrong et al. ......... 523/115

FOREIGN PATENT DOCUMENTS

| DE | 198 21 598 A1 | 11/1999 |
| EP | 0 555 807 A1 | 8/1993 |
| EP | 0 914 832 A1 | 5/1999 |
| WO | WO 01/41821 A1 | 6/2001 |

OTHER PUBLICATIONS

Muzzarelli, R. et al "Biological activitiy of chitosan . . . " Biomaterials (1988) vol. 9, pp. 247-252.*

T. Kawakami et al., "Experimental study on osteoconductive properties of a chitosan-bonded hydroxyapatite self-hardening paste," *Biomaterials* (1992), 13(11):759-763, Butterworth-Heinemann Ltd. Great Britain.

C. Zahraoui et al., "Influence of Sterilization on Injectable Bone Biomaterials," *Bone* (1999), 25(2):63S-65S, Elsevier Science, Inc.

* cited by examiner

*Primary Examiner*—Leigh C. Maier
(74) *Attorney, Agent, or Firm*—Foley & Lardner LLP

(57) ABSTRACT

By irradiating $^{60}$Co γ ray to chitin/chitosan, chitin/chitosan having high molecular weight is separated or decomposed into low molecular weight chitin/chitosan. A method of producing an osteoconduction substance comprises the steps of irradiating $^{60}$Co γ ray to chitin/chitosan to produce low molecular weight chitin/chitosan; preparing chitosan sol by dissolving low molecular weight chitin/chitosan in an acidic aqueous solution to obtain a chitosan acidic aqueous solution and kneading the chitosan acidic aqueous solution and apatite powder; and neutralizing the chitosan sol by the use of a neutralizing agent.

3 Claims, 3 Drawing Sheets

METHOD OF PRODUCING LOW MOLECULAR WEIGHT CHITIN/CHITOSAN AND METHOD OF PRODUCING AN OSTEOCONDUCTION SUBSTANCE

BACKGROUND OF THE INVENTION

This invention relates to a method of producing low molecular weight chitin/chitosan and a method of producing an osteoconduction substance and, in particular, to a method of producing low molecular weight chitin/chitosan by irradiation of $^{60}$Co γ (cobalt 60 gamma ray) and a method of producing an osteoconduction substance using the low molecular weight chitin/chitosan.

Generally, an osteoconduction substance is used in the field of dental treatment and orthopedics. The osteoconduction substance has a nature of helping or promoting creation of a new bone when it is filled in or around a bone. The osteoconduction substance is excellent in affinity to a tooth and a bone in a human body. The osteoconduction substance has a neutral pH value.

In an existing method of producing an osteoconduction substance, chitin/chitosan is at first dissolved in an acidic aqueous solution to obtain an acidic aqueous solution of chitosan as chitosan sol. The chitosan sol and apatite powder are kneaded together. An acid used in dissolving chitin/chitosan may be acetic acid, lactic acid, malic acid, citric acid, adipic acid, tartaric acid, malonic acid, stearic acid, succinic acid, maleic acid, aspartic acid, and glycin.

The chitosan sol with apatite powder kneaded therein is neutralized by an aqueous solution containing an alkaline compound, such as $CaCO_3$, ZnO, CaO, and CaOH. The chitosan sol after neutralized is solidified in 30 to 60 minutes into the osteoconduction substance having a pH value between 7.0 and 10.0. Thereafter, the osteoconduction substance is dehydrated and stored. The osteoconduction substance after dehydrated is a brittle material.

Prior to use, distilled water or physiological salt solution is absorbed into the osteoconduction substance in order to restore the osteoconduction substance into an elastic body such as rubber.

The osteoconduction substance thus produced is cut into a desired size corresponding to a diseased part of an organism. For example, after operation for periodontitis, the osteoconduction substance is inserted between a jaw bone and a gingiva around a resected site to reconstruct or reproduce the jaw bone.

In the osteoconduction substance containing apatite powder, the apatite powder is neither migrated nor lost. This is because the chitosan sol is transformed into gel so that the apatite powder is appropriately dispersed and fixedly confined in the osteoconduction substance. Before chitin/chitosan is absorbed into an organism, osteoid is effectively grown and substituted for a bone.

However, the existing osteoconduction substance requires a long time to create a new bone.

It is noted here that chitosan has a high molecular weight and is therefore water-insoluble and hardly absorbable into an organism. It is preferable to separate or decompose high molecular weight chitosan into low molecular weight chitosan. This is because chitosan tends to be absorbed by cells as its molecular weight decreases and, as a result, to activate osteoblast cells. For this purpose, chitosan is subjected to hydrolysis using dense hydrochloric acid. However, this technique requires severe and strict conditions. In addition, it is difficult to control the molecular weight of chitosan.

SUMMARY OF THE INVENTION

It is therefore an object of this invention to provide a method of producing low molecular weight chitosan, which is capable of separating or decomposing high molecular weight chitosan into low molecular weight chitosan by a simple operation.

It is another object of this invention to provide a method of producing an osteoconduction substance, which is capable of accelerating osteoconduction, i.e., creation of a new bone to shorten the time required therefor.

According to this invention, there is provided a method of producing low molecular weight chitin/chitosan, comprising the step of irradiating $^{60}$Co γ ray to chitin/chitosan to thereby separate or decompose chitin/chitosan into low molecular weight chitin/chitosan.

According to this invention, there is also provided a method of producing an osteoconduction substance, comprising the steps of irradiating $^{60}$Co γ ray to chitin/chitosan to produce low molecular weight chitin/chitosan, preparing chitosan sol by dissolving low molecular weight chitin/chitosan in an acidic aqueous solution to obtain a chitosan acidic aqueous solution and kneading the chitosan acidic aqueous solution and apatite powder, and neutralizing the chitosan sol by the use of a neutralizing agent.

According to this invention, there is also provided a method of producing an osteoconduction substance in the form of a film or a paste.

DESCRIPTION OF THE PREFERRED EMBODIMENT

Now, description will be made of a method of producing low molecular weight chitin/chitosan and a method of producing an osteoconduction substance according to one embodiment of this invention.

The method of producing low molecular weight chitin/chitosan comprises the step of irradiating $^{60}$Co γ ray (cobalt 60 gamma ray) to chitin/chitosan having a high molecular weight to separate or decompose high molecular weight chitin/chitosan into low molecular weight chitin/chitosan. For example, the molecular weight of the chitin/chitosan is lowered by irradiation at the dose of 27 kGy. Preferably, the dose of $^{60}$Co γ ray is within the range of 0.5 and 80 kGy (kilogiga), which is equivalent to that typically used in sterilization.

Thus, the molecular weight of chitin/chitosan can be divided and lowered by irradiation of $^{60}$Co γ ray without using a chemical agent.

Next, description will be made of the method of producing an osteoconduction substance, including the step of producing low molecular weight chitin/chitosan.

Figure 1:
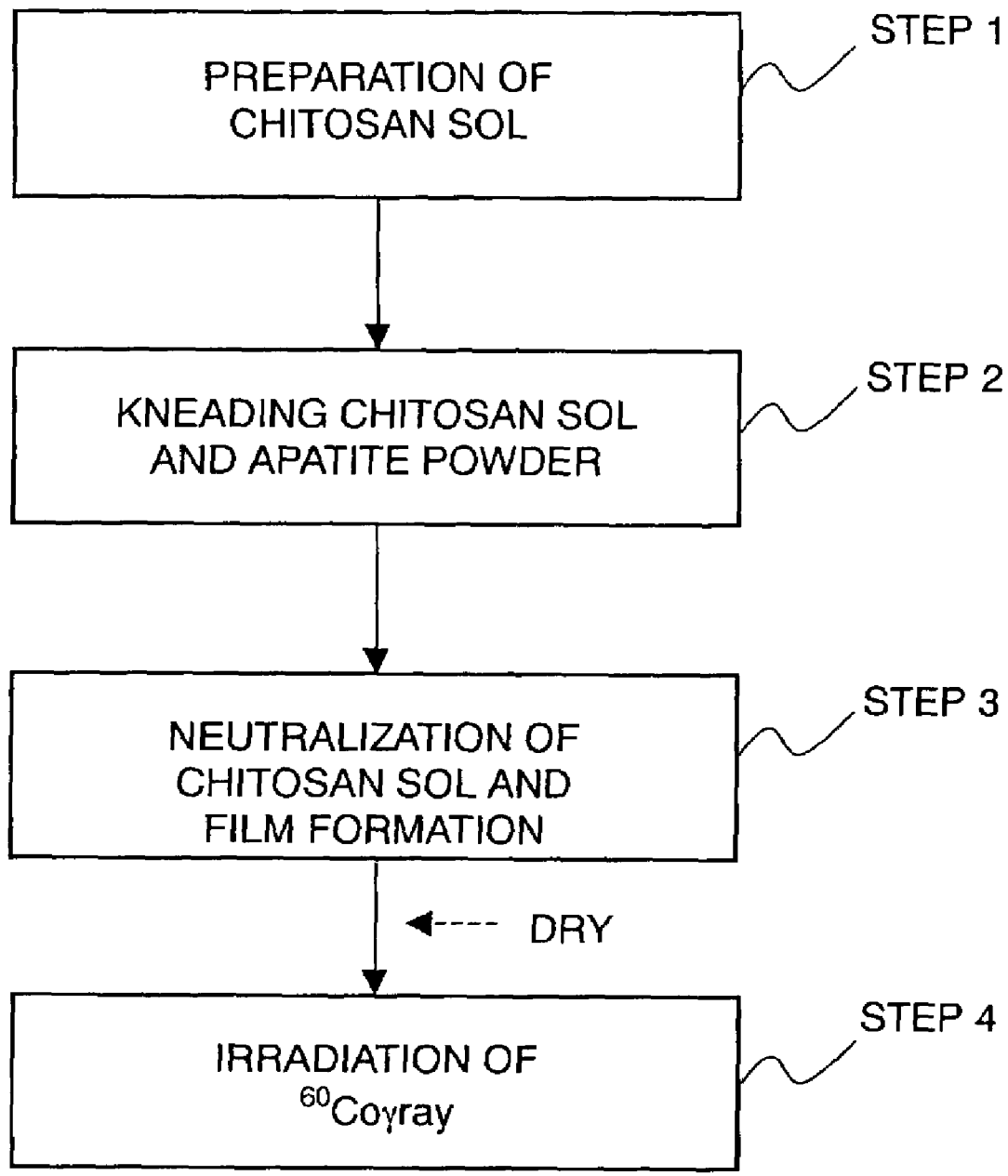
FIG. 1 is a flow chart for describing a method of producing low molecular weight chitosan and a method of producing an osteoconduction substance.

Referring to FIG. 1, the method of producing an osteoconduction substance comprises the steps of preparing an acidic aqueous solution of chitosan by distilled water or physiological saline solution, acid, and chitin/chitosan powder to produce chitosan sol (step 1) and kneading the chitosan sol and apatite powder (step 2). Thereafter, the chitosan sol with the apatite powder kneaded therein is stored or reserved in a container.

By neutralizing the chitosan sol with an aqueous solution containing a compound, the osteoconduction substance having a pH value between 6.0 and 8.0 is obtained (step 3). After neutralized by the aqueous solution, the osteoconduction substance in the form of a film or a paste with predetermined elastic strength is obtained after lapse of time. Then, the osteoconduction substance is irradiated by $^{60}$Co γ ray to produce low molecular weight chitin/chitosan (step 4).

For example, the osteoconduction substance is cut into a predetermined shape and implanted into a diseased part of an organism. The step of irradiating $^{60}$Co γ ray to produce low molecular weight chitin/chitosan may be carried out before the step 1 of preparing the chitosan sol. In other words, $^{60}$Co γ ray may be irradiated to chitin/chitosan powder.

As the apatite powder, use may be made of chemically synthesized hydroxyapatite. As the hydroxyapatite powder, use may be made of α-tricalcium phosphate or β-tricalcium phosphate. As the compound, use may be made of sodium chloride, sodium bicarbonate, sodium polyphosphate, and calcium oxide.

The osteoconduction substance may be dehydrated and thereafter sterilized by the use of an ethylene oxide gas. However, the osteoconduction substance after dehydration is brittle and may easily be damaged by external force.

In case where the osteoconduction substance is dehydrated, the osteoconduction substance must be restored into an elastic body such as rubber prior to implanting into the organism. Specifically, one of Ringer's solution, distilled water, and physiological saline solution is absorbed into the osteoconduction substance. For example, the osteoconduction substance is dipped in the Ringer's solution having a pH value between 6.0 and 10.0 for a predetermined time period (specifically, on the order between 5 and 10 minutes). The osteoconduction substance with the Ringer's solution absorbed therein is restored into an elastic body such as rubber.

Figure 2:
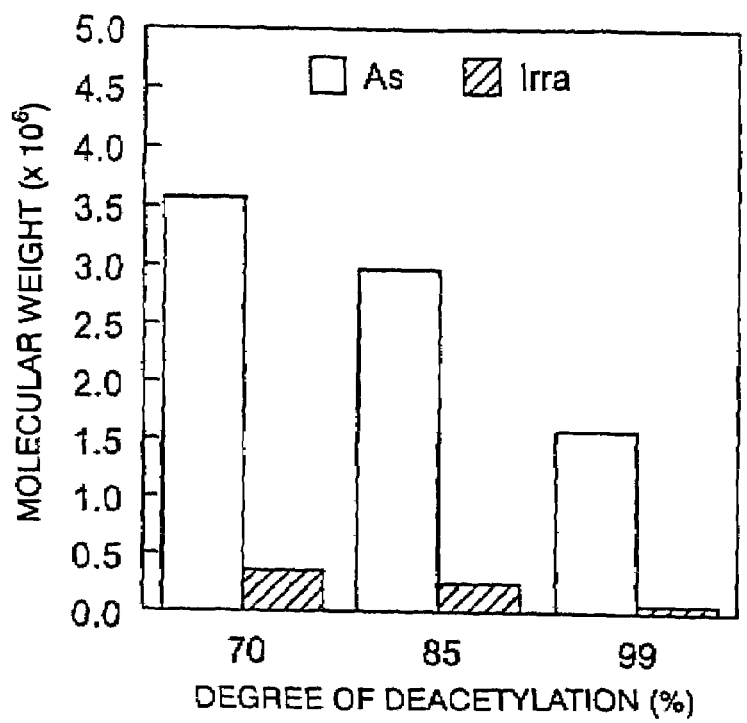
FIG. 2 is a graph showing the relationship between the molecular weight and the degree of deacetylation of chitin/chitosan.

Referring to FIG. 2, the molecular weight of chitin/chitosan is divided and reduced by irradiating $^{60}$Co γ ray to chitin/chitosan. In FIG. 2, the abscissa and the ordinate represent the degree of deacetylation and the molecular weight, respectively. As well known, chitosan is obtained by deacetylation of chitin. A higher degree of deacetylation represents a higher purity of chitosan. In the figure, AS and Irra represent unirradiated samples not irradiated by $^{60}$Co γ ray and irradiated samples irradiated by $^{60}$Co γ ray, respectively. As seen from FIG. 2, the irradiated samples are lower in molecular weight than the unirradiated samples.

In this specific example, the molecular weight of the chitin/chitosan was lowered by irradiation at the dose of 27 kGy. Preferably, the dose of $^{60}$Co γ ray is within the range of 0.5 and 80 kGy (kilogiga), which is equivalent to that typically used in sterilization.

Next, preparation was made of chitosan sol by dissolving chitin/chitosan with a 5% malic acid aqueous solution. Use was made of three kinds of chitin/chitosan with the degree of deacetylation of 70%, 85%, and 99%. The malic acid aqueous solution was prepared by the physiological saline solution of 2 cc and the malic acid of 0.1 g.

The chitosan sol was mixed and kneaded with 0.4 g of hydroxyapatite. The mixture was poured into a petri dish to the thickness of 0.5 mm and neutralized by 5% sodium polyphosphate solution to produce a film.

Figure 3:
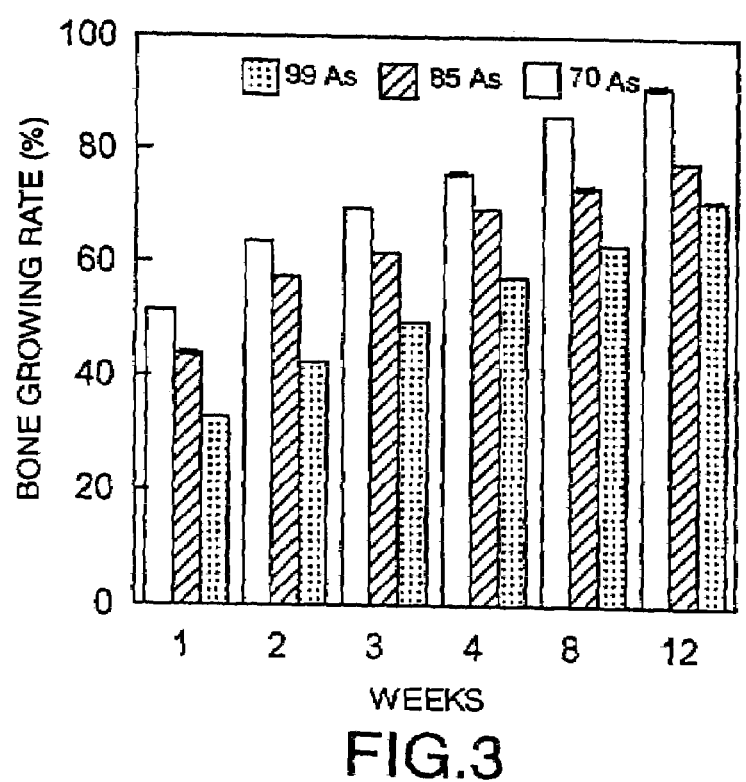
FIG. 3 is a graph showing the bone growing rate in case where an osteoconduction substance not irradiated by $^{60}$Co γ ray is used.
Figure 4:
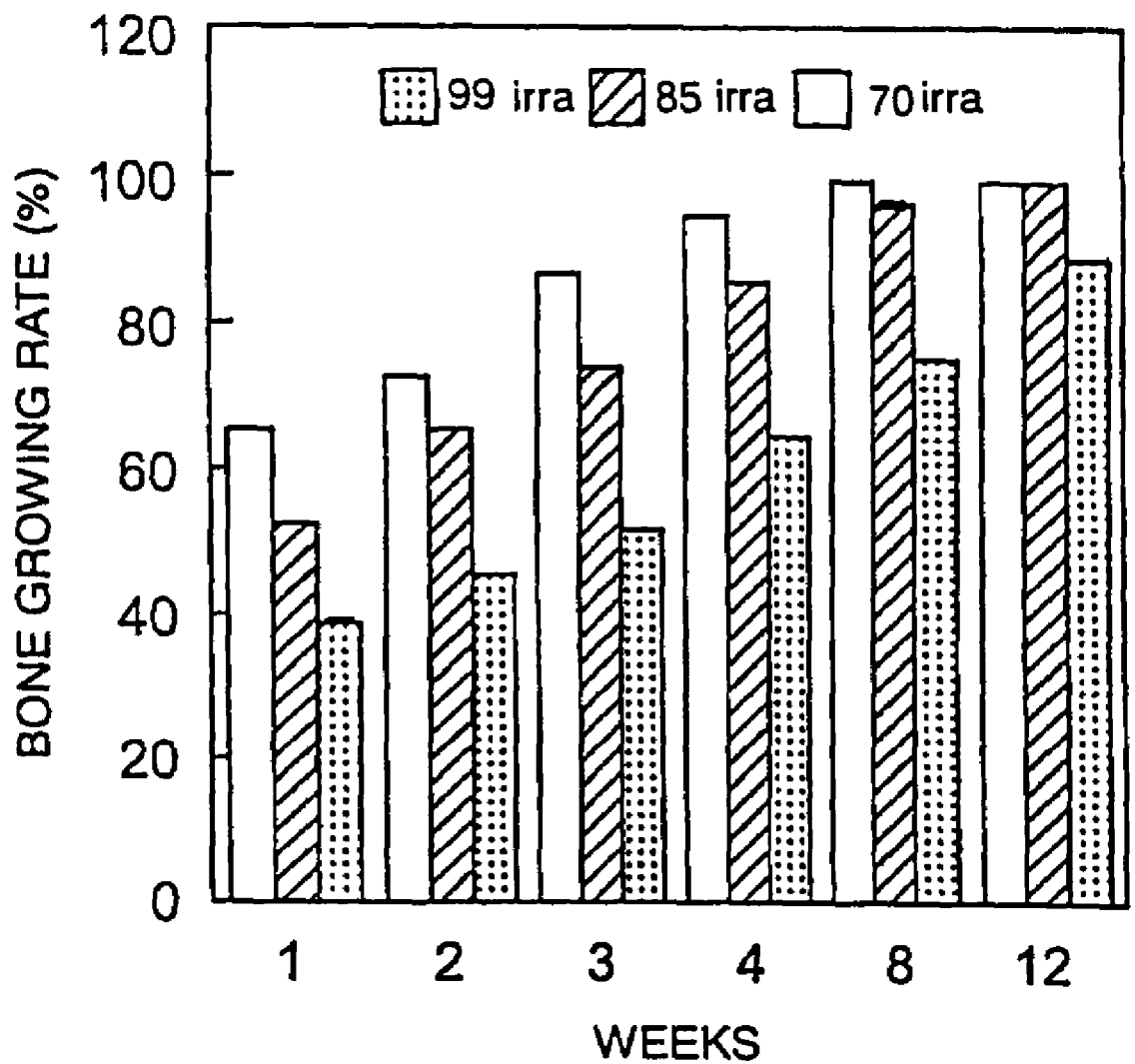
FIG. 4 is a graph showing the bone growing rate in case where an osteoconduction substance irradiated by $^{60}$Co γ ray is used.

Next, by the use of these films, an animal test was carried out. In the test, a cranial bone of each rat was drilled to form a recess having the depth of 0.2 mm, the length of 3.0 mm, and the width of 3.0 mm. The film was cut into the thickness of 0.2 mm, the length of 3.0 mm, and the width of 3.0 mm and implanted in the recess. Then, the rats were slaughtered after lapse of one, two, three, four, and eight weeks. From the rats, pathologic specimens were extracted and observed by a microscope. The result of observation is shown in FIGS. 3 and 4. FIG. 3 shows the result in case where the film not irradiated by $^{60}$Co γ ray was implanted into the cranial bone of the rat. FIG. 4 shows the result in case where the film irradiated by $^{60}$Co γ ray was implanted into the cranial bone of the rat.

In FIGS. 3 and 4, 70As, 85As, 99As represent the degree of deacetylation of 70%, 85%, and 99%, respectively.

For the sample using chitosan having the degree of deacetylation of 99%, the recess was completely filled by a new bone after lapse of 8 weeks. For the sample using chitosan having the degree of deacetylation of 85%, the recess was completely filled by a new bone after lapse of 12 weeks.

The unirradiated films were insufficient in bone creation as compared with the irradiated films.

Therefore, it is understood that the bone creation is promoted by irradiating $^{60}$Co γ ray to the film containing chitosan.

As described above, in the method of producing low molecular weight chitin/chitosan and the method of producing an osteoconduction substance according to this invention, high molecular weight chitin/chitosan can be separated or decomposed into low molecular weight chitin/chitosan by a simple operation of irradiating $^{60}$Co γ ray to chitin/chitosan without using a chemical agent.

In the method of producing the osteoconduction substance according to this invention, it is possible to shorten the time required for bone creation by irradiating $^{60}$Co γ ray to chitin/chitosan in order to separate or decompose high molecular weight chitin/chitosan into low molecular weight chitin/chitosan.

What is claimed is:

1. A method of producing an osteoconduction substance and for using same in the creation of a new bone, comprising, in order, the steps of:
   preparing chitosan sol by dissolving said chitin/chitosan in an acidic aqueous solution to obtain a chitosan acidic aqueous solution;
   kneading the chitosan acidic aqueous solution with an apatite powder; and
   neutralizing the chitosan sol by the use of a neutralizing agent to form the osteoconduction substance;
   irradiating the osteoconduction substance with $^{60}$Co γ rays to produce a lower molecular weight osteoconduction substance as compared to non-irradiated osteoconduction substance; and
   applying the produced osteoconduction substance to a subject to stimulate production of a new bone in the area of application.

2. The method of claim 1 further including the step of storing the acidic aqueous solution with an apatite powder kneaded therein prior to the neutralizing step.

3. A method comprising the steps of:
producing an osteoconduction substance for the creation of a new bone, and
stimulating the time for the creation of new bone; said step of stimulating including, in order, the steps of:
preparing chitosan sol by dissolving said chitin/chitosan in an acidic aqueous solution to obtain a chitosan acidic aqueous solution;
kneading the chitosan acidic aqueous solution with an apatite powder; and
neutralizing the chitosan sol into the osteoconduction substance by the use of a neutralizing agent;
irradiating the osteoconduction substance with $^{60}$Co γ rays to produce a lower molecular weight osteoconduction substance as compared to non-irradiated osteoconduction substance; and applying the produced osteoconduction substance to a subject to stimulate production of a new bone in the area of application.

\* \* \* \* \*